United States Patent
Bardonnaud et al.

(10) Patent No.: US 10,456,355 B1
(45) Date of Patent: Oct. 29, 2019

(54) PHARMACEUTICAL HYDROCORTISONE SOLUTION FOR AN INJECTION DEVICE

(71) Applicant: CROSSJECT, Dijon (FR)

(72) Inventors: Pauline Bardonnaud, Dijon (FR); Frédérique Flores-Ivanez, Ruffey les Beaune (FR)

(73) Assignee: CROSSJECT, Dijon (FR)

( * ) Notice: Subject to any disclaimer, the term of this patent is extended or adjusted under 35 U.S.C. 154(b) by 0 days.

(21) Appl. No.: 16/343,163

(22) PCT Filed: Oct. 25, 2017

(86) PCT No.: PCT/FR2017/052941
§ 371 (c)(1),
(2) Date: Apr. 18, 2019

(87) PCT Pub. No.: WO2018/078285
PCT Pub. Date: May 3, 2018

(30) Foreign Application Priority Data

Oct. 26, 2016 (FR) ..................... 16 60393

(51) Int. Cl.
| | |
|---|---|
| *A61K 31/56* | (2006.01) |
| *A61K 31/16* | (2006.01) |
| *A61K 9/00* | (2006.01) |
| *A61K 31/573* | (2006.01) |
| *A61K 31/10* | (2006.01) |
| *A61K 47/20* | (2006.01) |
| *A61M 5/30* | (2006.01) |
| *A61K 47/02* | (2006.01) |
| *A61K 47/18* | (2017.01) |

(52) U.S. Cl.
CPC ............ *A61K 9/0019* (2013.01); *A61K 31/10* (2013.01); *A61K 31/573* (2013.01); *A61K 47/02* (2013.01); *A61K 47/183* (2013.01); *A61K 47/20* (2013.01); *A61M 5/30* (2013.01)

(58) Field of Classification Search
CPC .............................. A61K 31/56; A61K 31/16
USPC .................................................. 514/178, 578
See application file for complete search history.

(56) References Cited

FOREIGN PATENT DOCUMENTS

| | | |
|---|---|---|
| FR | 2 807 946 A1 | 10/2001 |
| FR | 2 815 544 A1 | 4/2002 |
| WO | 01/078810 A1 | 10/2001 |
| WO | 2015/092758 A1 | 6/2015 |

OTHER PUBLICATIONS

Efcortesol Injection, Amdipharm UK Ltd.: "Efcortesol Injection", Authorisation No. PL 20072/0229, 2009, pp. 1-10, XP055375071, Retrieved from the Internet: URL:http://www.mhra.gov.uk/home/groups/spcpil/documents/spcpi1/con1492496656049.pdf, [retrieved on May 22, 2017].
Mar. 14, 2018 Search Report issued in International Patent Application No. PCT/FR2017/052941.

*Primary Examiner* — Raymond J Henley, III
(74) *Attorney, Agent, or Firm* — Oliff PLC

(57) ABSTRACT

A pharmaceutical hydrocortisone solution including at least hydrocortisone or a pharmaceutically-acceptable salt thereof, rongalite, disodium EDTA, and a solvent. Also relates to its use in the treatment of acute adrenal insufficiency and asthma. Also relates to an injection kit including an injection device and this pharmaceutical solution.

13 Claims, No Drawings

PHARMACEUTICAL HYDROCORTISONE SOLUTION FOR AN INJECTION DEVICE

The invention concerns a pharmaceutical solution of hydrocortisone or of a pharmaceutically-acceptable salt thereof (hereinafter abbreviated as «pharmaceutical hydrocortisone solution») intended to be injected by parenteral, in particular intramuscular, route.

Hydrocortisone and hydrocortisone salts are known to be used as anti-inflammatory agents. It is common to use these active substances in particular in the treatment of asthma, endocrine disorders, dermatological disorders and allergic states, as well as acute adrenal insufficiency.

Hydrocortisone and its salts belong to the corticosteroids family.

Hydrocortisone, as well as its salts, are sensitive to oxidation. This is why the pharmaceutical solutions of these active substances always comprise at least one antioxidant. However, the antioxidants themselves implemented in these pharmaceutical solutions are unstable.

This is why, it is known that these pharmaceutical solutions comprise a $2^{nd}$ antioxidant which is disodium ethylenediaminetetraacetic acid (hereinafter abbreviated as «disodium EDTA»). The function of disodium EDTA is to stabilize (or in other words protect) the antioxidant which, in turn, is selected to protect hydrocortisone thereby preserving it from oxidation.

For example, there is known the pharmaceutical product commercialized by the company AMDIPHARM under the commercial name Efcortesol® which is a pharmaceutical solution of hydrocortisone sodium phosphate at a concentration of 13.39% m/v (in other words there are 13.39 g of this salt in 100 mL of solution). This product is conditioned either in 1 mL ampoules which contain 100 mg of hydrocortisone, or in 5 mL ampoules which contain 500 mg of hydrocortisone.

Efcortesol® further comprises:
two antioxidants: disodium EDTA which also serves as a chelating agent and formaldehyde sodium bisulfite which is also an antimicrobial, as well as
sodium hydrogen phosphate, sodium dihydrogen phosphate, phosphoric acid (concentrated at 10% of volume),
water for an injectable preparation.

However, formaldehyde sodium bisulfite is not on the GRAS list («GRAS» being the acronym of «Generally Recognized As Safe») of the FDA («FDA» being the acronym of «Food and Drug Administration», namely the American authority for surveillance of food and drugs).

In addition, this antioxidant is not described in the international reference book referring to pharmaceutical excipients which is the «Handbook of pharmaceutical excipients».

Moreover, in order to comply with the necessary dose of the therapeutic indication (for example an acute adrenal insufficiency, asthma or any disease requiring rapidly taking a considerable amount of a corticosteroid) during an intramuscular injection which involves a smaller injected volume, a higher concentration of the pharmaceutical solution than that proposed by the pharmaceutical product Efcortesol® may be required.

This is why, it would be desirable to provide a new pharmaceutical solution of hydrocortisone or of a pharmaceutically-acceptable salt thereof which could be more concentrated than the known solution Efcortesol® and which is perfectly stable over time. It would be advantageous that the profile of impurities is close to this known solution of Efcortesol® and that it has, whenever possible, a minimum of unknown impurities for which a characterization and a tedious toxicity study would be necessary.

The inventors of the present invention have sought to develop a new pharmaceutical solution of hydrocortisone or of a pharmaceutically-acceptable salt thereof intended to be injected by parenteral, in particular intramuscular, route which replaces formaldehyde sodium bisulfite with another antioxidant, said solution should:
have a level of impurities which at most equal to, preferably lower than, the level of impurities of Efcortisol® considered as a reference pharmaceutical product, and
be devoid of any unknown impurity in a considerable amount which would require a characterization.

The inventors of the present invention have quite surprisingly discovered that the association of the two antioxidants which are rongalite (also known under the name of «sodium formaldehyde sulfoxylate») and disodium EDTA in a pharmaceutical solution of hydrocortisone or of a pharmaceutically-acceptable salt thereof would perfectly allow reaching these objectives.

A first object of the present invention is a pharmaceutical hydrocortisone solution which comprises at least:
hydrocortisone or a pharmaceutically-acceptable salt thereof;
rongalite;
disodium EDTA;
a solvent.

The association of the two antioxidants which are disodium EDTA and rongalite confers the hydrocortisone solution with a perfectly remarkable stability over time, which is equivalent to, and even better than, that of the reference product Efcortesol®.

Furthermore, rongalite is an excipient which is perfectly authorized by the pharmaceutical administrations.

Finally, it has been observed that a pharmaceutical solution according to the invention has a level of impurities which is close to that of the reference product Efcortesol®, and even lower than the latter, and that under various and forced storage conditions (namely temperature and relative humidity).

Hence, the present invention lies in the selection of an association of two specific antioxidants to stabilize a pharmaceutical hydrocortisone solution. Thus, the invention concerns the association of two antioxidants which are disodium EDTA and rongalite to stabilize a pharmaceutical hydrocortisone solution.

The pharmaceutically-acceptable salt of hydrocortisone may be selected from hydrocortisone sodium phosphate, hydrocortisone sodium succinate, hydrocortisone hydrogen succinate, hydrocortisone butyrate and hydrocortisone acetate.

Preferably, the salt of hydrocortisone is hydrocortisone sodium phosphate.

The solvent may be any pharmaceutically-acceptable solvent which is compatible with hydrocortisone and its salts, as well as any other compound comprised in said pharmaceutical solution according to the invention. It may consist of water, in particular water used in injection devices (in other words, water for an injectable preparation), as well as water containing isotonising additives or solutions of sodium chloride. Water for injectable preparations is ultrapure and devoid of bacterial contaminants.

The pharmaceutical solution may further comprise at least one buffer. For example, it may consist of a buffer selected from sodium acetate, sodium citrate, sodium dihydrogen phosphate and sodium hydrogen phosphate.

Preferably, the buffer is selected from sodium dihydrogen phosphate and sodium hydrogen phosphate.

In one embodiment of the invention, the pharmaceutical solution comprises as buffers sodium dihydrogen phosphate and sodium hydrogen phosphate.

The pH of the pharmaceutical solution is advantageously comprised between 7 and 9, preferably between 7.5 and 8.5.

Said pharmaceutical solution may further comprise at least one pharmaceutically-acceptable excipient.

In one embodiment of the invention, the pharmaceutical solution comprises:
hydrocortisone sodium phosphate;
rongalite;
disodium EDTA;
at least one buffer;
a solvent, preferably water for an injectable preparation.

Preferably, in this embodiment of the invention, the pharmaceutical solution comprises as buffers sodium dihydrogen phosphate and sodium hydrogen phosphate.

Advantageously, the concentration of hydrocortisone in said pharmaceutical solution is comprised between 150 mg/mL and 170 mg/mL.

In a quite preferable manner, the concentration of hydrocortisone in said solution is 160 mg/mL.

The pharmaceutical solution according to the invention may comprise in g for 200 mL of the solution:
between 20 g and 60 g, preferably between 40 g and 45 g, of hydrocortisone or of a pharmaceutically-acceptable salt thereof;
between 0.2 g and 1.2 g, preferably between 0.3 g and 0.5 g, of rongalite;
between 0.1 g and 0.6 g, preferably between 0.15 g and 0.25 g, of disodium EDTA;
between 160 g and 200 g, of solvent, preferably water for an injectable preparation.

Said solution may further comprise up to 10 g of at least one pharmaceutically-acceptable excipient.

An object of the present invention is also a method for preparing the pharmaceutical solution according to the invention as described hereinabove, which comprises at least the following steps of:
a) preparing under stirring a mixture comprising at least the solvent, rongalite and disodium EDTA;
b) adding under stirring hydrocortisone or a pharmaceutically-acceptable salt thereof so as to obtain said pharmaceutical solution;
c) optionally, performing at least one filtration step on the pharmaceutical solution obtained on completion of step b).

In the case where the pharmaceutical solution comprises buffers, these buffers are advantageously mixed together prior to step a) before being added to the mixture of step a).

When the pharmaceutical solution comprises at least one pharmaceutically-acceptable excipient, this excipient may be added to the mixture of step a).

Throughout the preparation method, the steps implementing stirring are advantageously carried out at a stirring speed comprised between 200 and 400 rpm, more preferably between 250 and 300 rpm.

The filtration step may comprise at least one filtration selected from a clarifying filtration and a sterilizing filtration.

Preferably, the filtration step consists of a clarifying filtration followed by a sterilizing filtration.

An object of the invention is also the pharmaceutical solution as described hereinabove for its use in the treatment of diseases selected from acute adrenal insufficiency, asthma or any disease requiring rapidly taking a considerable amount of a corticosteroid. Preferably, it consists of the treatment of acute adrenal insufficiency and asthma.

Said solution is advantageously administrated by parenteral route, preferably by intramuscular route.

An object of the present invention is also an injection kit, preferably a kit for injection by intramuscular route, including:
an injection device;
the pharmaceutical solution according to the invention as described hereinabove.

Advantageously, the injection volume of the injection device is comprised between 0.60 mL and 0.65 mL.

Said injection device may be intended to be disposable. For example, it consists of a ready-to-use pre-filled tube.

In a preferred embodiment of the invention, said device is a disposable pre-filled injection device, needleless and automatic thanks to a gas generator which equips it. It may consist of a needleless injection device with a pyrotechnic cartridge. In this respect, the patent applications FR 2 815 544 A1 and FR 2 807 946 A1 describe an example of this injection device.

In a quite advantageous manner, the injection device is a device commercialized by the company Crossject under the commercial name ZENEO®.

Thus, in one embodiment of the injection kit according to the invention, the injection device is a needleless injection device with a pyrotechnic cartridge.

EXPERIMENTAL PART

Experiments have been carried out in order to compare the impurities content of three solutions of hydrocortisone sodium phosphate. Two of the solutions were solutions called «comparative» solutions (hereinafter called «comparative 1» and «comparative 2») and the $3^{rd}$ solution was a solution according to the invention (hereinafter called «invention»).

More specifically, the comparative solutions 1 and 2 differ from the solution of the invention in that they are devoid of rongalite which is replaced respectively with formaldehyde sodium bisulfite and sodium metabisulfite.

The comparative solution 1 comprised the same association of antioxidants (that is to say disodium EDTA and formaldehyde sodium bisulfite) as the pharmaceutical product Efcortesol®, namely the reference product the present invention aims at presenting a level of impurities which is at most equal to, preferably lower than, the level of impurities of this product.

Table 1 below details for each of the 3 prepared solutions the weight percentages of each of the constituents (except water) expressed relative to the total weight of the considered solution.

TABLE 1 detailing the weight percentages of the constituents of the comparative solutions 1 and 2 and the invention

|  | Comparative 1 | Comparative 2 | Invention |
|---|---|---|---|
| hydrocortisone sodium phosphate | 20.42 | 20.42 | 20.42 |
| disodium EDTA | 0.08 | 0.08 | 0.08 |
| rongalite | 0 | 0 | 0.16 |
| formaldehyde sodium bisulfite | 0.16 | 0 | 0 |
| metabisulfite | 0 | 0.16 | 0 |
| Buffer solution: water for an injectable preparation | Q.S. 100 ml | Q.S. 100 ml | Q.S. 100 ml |

TABLE 1-continued detailing the weight percentages of the constituents of the comparative solutions 1 and 2 and the invention

|  | Comparative 1 | Comparative 2 | Invention |
|---|---|---|---|
| comprising the buffers: | | | |
| sodium hydrogen phosphate: | 0.27 | 0.27 | 0.27 |
| sodium dihydrogen phosphate: | 0.01 | 0.01 | 0.01 |

In Table 1, Q.S. is the abbreviation of «Quantum Satis» meaning that the amount of buffer solution is such that the volume of the solution is completed to 100 mL.

In these solutions, the concentration of hydrocortisone was 160 mg/mL.

The comparative solutions 1 and 2 and the invention have all been prepared in the following manner:

a) we have prepared under stirring, using a magnetic stirrer at 250 rpm, a mixture containing sodium dihydrogen phosphate and sodium hydrogen phosphate, b) we have added under stirring, using a magnetic stirrer at 300 rpm, water, the two antioxidants (namely disodium EDTA and rongalite, formaldehyde sodium bisulfite and metabisulfite, respectively for the solutions according to the invention, the comparative solution 1 and the comparative solution 2), and we have resumed stirring for 9 minutes;

c) we have added under stirring, using a magnetic stirrer at 300 rpm, hydrocortisone sodium phosphate and we have resumed stirring until complete dissolution of this salt so as to obtain a solution;

d) we have performed a step of clarifying filtration at a rate of 250 mL/minute on the solution obtained at step c), followed by a step of sterilizing filtration at a pressure of 56 Pa at a rate of 140 mL/minute;

e) we have bubbled with nitrogen the solution obtained at step d).

Bubbling with nitrogen consists of a partial inerting which allows reducing the contact of the pharmaceutical solution with oxygen and therefore limiting the oxidation of said solution.

The three solutions thus obtained, that is to say the comparative solutions 1, 2 and invention have been conditioned in glass tubes equipped with two stoppers at their ends.

More specifically, the tubes have been filled with 0.65 mL of the solution. Nitrogen flushing has been applied to the surface of the solutions in order to clear oxygen present in the head space of these tubes. Finally, the tubes have been closed.

After one month of storage under a 75% relative humidity and at temperatures of 40° C. and 50° C., the area percentages of the impurities in each of the three solutions have been determined from analyses by high-performance liquid chromatography (hereinafter abbreviated as «HPLC»).

These area percentages are expressed relative to the area of the main peak of the considered solution (namely the comparative solutions 1 and 2 and the invention).

The HPLC analyses have been carried out under the following conditions:

a column commercialized by the company Phenomenex under the commercial name Luna® C18(2) with a 5 µm thickness and with dimensions (250×4.6) mm;
a rate of 1.5 mL/minute;
an injection volume of 5 µL;
an ultraviolet detector with a variable wavelength comprised between 190 and 400 nm or a photodiode detector;
a wavelength of 254 mm;
a temperature of the column of 25° C. (+/−) 2° C.;
a sample at ambient temperature;
a movable phase A: 0.1% (v/v) of trifluoroacetic acid in purified water;
a movable phase B: 0.1% (v/v) of trifluoroacetic acid in acetonitrile.

Table 2 below details the composition of the movable phase over time.

| Time (minutes) | Phase A (%) | Phase B (%) |
|---|---|---|
| 0 | 85 | 15 |
| 10 | 85 | 15 |
| 22 | 55 | 45 |
| 38 | 30 | 70 |
| 38.1 | 85 | 15 |
| 43 | 85 | 15 |

Table 3 below details the sum of the percentages of the impurities and the number of impurities for the solutions that have been stored at 40° C. for 1 month.

TABLE 3 details the area percentages of the impurities in the comparative solutions 1 and 2 and the invention stored at 40° C. under a 75% relative humidity

|  | Comparative 1 | Comparative 2 | Invention |
|---|---|---|---|
| sum of the impurities | 0.58% (6 impurities) | 0.21% (2 impurities) | 0.34% (4 impurities) |

The profile of impurities of the solution according to the invention is better than that of the comparative solution 1. Furthermore, with the solution according to the invention, no impurity higher than 0.2% has been detected.

Table 4 below details the area percentages of the aforementioned impurities for the solutions that have been stored at 50° C. for 1 month.

TABLE 4 detailing the area percentages of the impurities in the comparative solutions 1 and 2 and the invention stored at 50° C. under a 75% relative humidity

|  | Comparative 1 | Comparative 2 | Invention |
|---|---|---|---|
| sum of the impurities | 1.35% (7 impurities) | 1.18% (5 impurities including one higher than 0.2%) | 1.12% (6 impurities) |
| main unknown impurity | 0.23% | 0.35% | 0.24% |

In light of the results detailed in Table 4, we notice that the solution according to the invention has the least impurities: 1.12% against 1.18% and 1.35% (1.35 being the percentage of impurities of the reference product).

Thus, the solution according to the invention has a better stability than the comparative solution 1 whether at 40° C. or at 50° C.

In addition, in comparison with the comparative solution 2, the solution according to the invention has a much better stability under the most drastic conditions, namely 50° C.; which is very advantageous.

Thus, these solutions show that the association of the two antioxidants which are disodium EDTA with rongalite into a solution of hydrocortisone sodium phosphate allows obtaining pharmaceutical solutions according to the invention which are perfectly stable over time. Indeed, the pharmaceutical solutions according to the invention have a level of impurities which is lower than the reference product which is Efcortesol®.

In addition, within 6 months of storage at 40° C., the area percentage of the sum of the impurities of the solution according to the invention was 1.65%. This result is quite satisfactory, considering that the maximum specification is 2% and that hydrocortisone sodium phosphate is also very sensitive to temperature.

Table 5 below details the area percentages of the sum of the impurities over time of the solution according to the invention that has been stored at 25° C. under a 60% relative humidity.

TABLE 5 detailing the area percentages of the impurities in the
solution according to the invention stored
at 25° C. under a 60% relative humidity over time

| Time (month) | 0 | 1 | 2 | 3 | 6 |
|---|---|---|---|---|---|
| sum of the impurities | 0.04% | 0.04% | 0.05 | 0.11 | 0.16 |

In light of the results detailed in Table 5, we notice that the profile of impurities of the solution according to the invention is perfect, in comparison with a maximum specification of 2%.

These experimental results show that the pharmaceutical solutions of hydrocortisone according to the invention are stable over time, and this even under forced conditions (that is to say with a high hygrometry, under a 60% or 75% relative humidity, and at high temperatures of 40° C. or 50° C.).

The invention claimed is:

1. A pharmaceutical hydrocortisone solution which comprises at least:
   hydrocortisone or a pharmaceutically-acceptable salt thereof;
   rongalite;
   disodium ethylenediaminetetraacetic acid (disodium EDTA);
   a solvent.

2. The pharmaceutical solution according to claim 1, wherein the pharmaceutically-acceptable salt of hydrocortisone is selected from hydrocortisone sodium phosphate, hydrocortisone sodium succinate, hydrocortisone hydrogen succinate, hydrocortisone butyrate and hydrocortisone acetate.

3. The pharmaceutical solution according to claim 2, wherein the pharmaceutically-acceptable salt of hydrocortisone is hydrocortisone sodium phosphate.

4. The pharmaceutical solution according to claim 1, wherein it further comprises at least one buffer.

5. The pharmaceutical solution according to claim 4, wherein the buffer is selected from sodium acetate, sodium citrate, sodium dihydrogen phosphate and sodium hydrogen phosphate.

6. The pharmaceutical solution according to claim 1, wherein the pH of the pharmaceutical solution is comprised between 7 and 9.

7. The pharmaceutical solution according to claim 1, wherein the concentration of hydrocortisone in said pharmaceutical solution is comprised between 150 mg/mL and 170 mg/mL.

8. The pharmaceutical solution according to claim 1, wherein it comprises in g for 200 mL of the solution:
   between 20 g and 60 g, of hydrocortisone or of a pharmaceutically-acceptable salt thereof;
   between 0.2 g and 1.2 g, of rongalite;
   between 0.1 g and 0.6 g, of disodium EDTA;
   between 160 g and 200 g, of solvent for an injectable preparation.

9. A method for preparing the pharmaceutical solution according to claim 1, wherein it comprises at least the following steps of:
   a) preparing under stirring a mixture comprising at least the solvent, rongalite and disodium EDTA;
   b) adding under stirring hydrocortisone or a pharmaceutically-acceptable salt thereof so as to obtain said pharmaceutical solution;
   c) optionally, performing at least one filtration step on the pharmaceutical solution obtained on completion of step b).

10. The pharmaceutical solution according to claim 1 for its use in the treatment of acute adrenal insufficiency and asthma.

11. The pharmaceutical solution according to claim 10, wherein said solution is administrated by parenteral route.

12. An injection kit, including:
   an injection device;
   the pharmaceutical solution according to claim 1.

13. The injection kit according to claim 12, wherein the injection device is a needleless injection device with a pyrotechnic cartridge.

* * * * *